(12) United States Patent
Litvin et al.

(10) Patent No.: US 9,138,390 B2
(45) Date of Patent: Sep. 22, 2015

(54) PETROLATUM BASED COMPOSITION COMPRISING GREATER THAN 10% SILICONE FOR IMPROVED FEEL WHILE REMAINING STABLE

(75) Inventors: Tamara Litvin, Woodbridge, CT (US); Joseph Oreste Carnali, Newtown, CT (US); Qiu Qiang, Trumbull, CT (US); Alexander Lips, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 786 days.

(21) Appl. No.: 12/423,984

(22) Filed: Apr. 15, 2009

(65) Prior Publication Data

US 2010/0266522 A1    Oct. 21, 2010

(51) Int. Cl.
| | |
|---|---|
| *A61K 8/36* | (2006.01) |
| *A61K 8/89* | (2006.01) |
| *A61K 8/31* | (2006.01) |
| *A61K 8/891* | (2006.01) |
| *A61Q 19/00* | (2006.01) |

(52) U.S. Cl.
CPC . *A61K 8/361* (2013.01); *A61K 8/31* (2013.01); *A61K 8/891* (2013.01); *A61Q 19/00* (2013.01); *A61K 2800/592* (2013.01)

(58) Field of Classification Search
CPC .................. A61K 8/361; A61K 2800/592
See application file for complete search history.

(56) References Cited

U.S. PATENT DOCUMENTS

| | | | |
|---|---|---|---|
| 3,298,919 A | 1/1967 | Bishop, Jr. et al |
| 5,266,321 A | 11/1993 | Shukuzaki et al. |
| 5,308,526 A | 5/1994 | Dias et al. |
| 5,336,692 A | 8/1994 | Gans et al. |
| 5,387,417 A | 2/1995 | Rentsch |
| 5,494,657 A | 2/1996 | Swenson |
| 5,558,872 A | 9/1996 | Jones et al. |
| 5,622,793 A | 4/1997 | Tijima et al. |
| 5,643,899 A | 7/1997 | Elias et al. |
| 5,744,146 A | 4/1998 | Peters et al. |
| 5,792,467 A | 8/1998 | Emerson et al. |
| 5,849,314 A | 12/1998 | Dobkowski et al. |
| 5,851,978 A | 12/1998 | Shana'a |
| 6,180,127 B1 | 1/2001 | Calton et al. |
| 6,238,682 B1 | 5/2001 | Klofta et al. |
| 6,264,963 B1 | 7/2001 | Leifheit et al. |
| 6,419,938 B1 | 7/2002 | Riedel et al. |
| 6,524,562 B2 | 2/2003 | Guskey |
| 6,555,099 B2 | 4/2003 | Guskey et al. |
| 6,582,683 B2 | 6/2003 | Jezior |
| 6,784,144 B2 | 8/2004 | James |
| 2002/0119897 A1 | 8/2002 | James |
| 2004/0202624 A1 | 10/2004 | Pflecker et al. |
| 2006/0165626 A1 | 7/2006 | Ricard et al. |
| 2007/0032393 A1 | 2/2007 | Patel et al. |

FOREIGN PATENT DOCUMENTS

| | | |
|---|---|---|
| CN | 1152866 A | 6/1997 |
| EP | 80819428 A2 | 1/1998 |
| GB | 998 706 A | 7/1965 |
| WO | WO9951192 | 10/1999 |
| WO | WO2010119034 A2 | 10/2010 |

OTHER PUBLICATIONS

Co-pending application for: Applicant Litvin et al.; U.S. Appl. No. 12/423,987, filed Apr. 15, 2009, entitled: Composition Comprising Silicone Oil or Oils Structured with Copolymers Carrying Greater than 70% Long Chain Alkyl Group.
International Search Report and Written Opinion on Application No. PCT/EP2010/0054831 dated Apr. 26, 2011.
Bockisch, Fats and Oils, Fats and Oils, Jan. 1, 1998, 506, US.

*Primary Examiner* — Jeffrey S. Lundgren
*Assistant Examiner* — Sara E Townsley
(74) *Attorney, Agent, or Firm* — Ronald A. Koatz

(57) ABSTRACT

The present invention discloses petrolatum based composition containing silicone oils which are structured with specific blend and ratio of fatty acids.

12 Claims, 5 Drawing Sheets

Molecular structure of Ganex V220 (PVP-eicosane copolymer)

PETROLATUM BASED COMPOSITION COMPRISING GREATER THAN 10% SILICONE FOR IMPROVED FEEL WHILE REMAINING STABLE

FIELD OF THE INVENTION

The present invention relates to petrolatum based compositions (i.e., having ≥50% petrolatum) comprising relatively large amounts of silicone oils. Although silicone oils improve greasy or tacky feel associated with petrolatum-based compositions, use of significant amount of silicone (e.g., >10%) results in instability as the silicone tends to separate out as a clear layer over time (e.g., too much silicone can dilute the structure of petrolatum so it can't "hold" the silicone). The present invention relates to petrolatum based compositions in which the silicone is structured by a specific blend of fatty acids (typically, in the art the silicones are structured using silicone-based elastomers). Using fatty acid to structure silicones utilized in a petrolatum base (by selecting correct blend and amount of fatty acid) permits the silicone to be incorporated into petrolatum (i.e., at levels of >10% by wt. silicone) without stability problems. Thus there is improved sensory (e.g., diminishing greasy feel) of the petrolatum because of presence of silicone, while simultaneously overcoming stability issues (e.g., phase stability) normally encountered at these levels of silicone.

In a separate application filed on the same date as this, applicants claim "structured" silicone compositions in which the silicone is structured with copolymers (e.g., of vinylpyrrolidone or other) carrying greater than 70% long chain alkyl groups (e.g., alpha olefins, such as eicosane are preferred), optionally further structured with fatty acids. The level of copolymer in silicone of that application is about 1 to 30%. Typically such copolymer structured silicone would not be used with petrolatum to structure the petrolatum (e.g., would be used to structure other types of oil instead) since too much of the polymer could cause petrolatum to become "stringy". In the petrolatum based compositions of the subject invention, the structured silicone, as noted, contains specific fatty acid blend to help stability. The silicone may optionally comprise a small amount of the copolymers bearing high amounts of long chain alkyl (e.g., vinylpyrrolidone/olefin copolymers) which are required in the other case to enhance sensory (it is believed this helps in formation of small round crystals). If too much polymer is used (typically >5% by weight of the petrolatum), the petrolatum becomes stringy and viscous and will not have ideal spreadability.

BACKGROUND

Petrolatum based compositions (i.e., composition in which the emollient petrolatum comprises greater than or equal to 50% of the composition) are desirable because of the excellent moisturization properties provided by petrolatum. However, it has sensory negatives perceived by consumers. Specifically, because of the oily/greasy and "tacky" (i.e., slightly adhesive or gummy to touch) feel, petrolatum has certain limits to the scope of application.

Silicone oil can improve the sensory aesthetics (oiliness; tackiness) of such petrolatum-based compositions, but use of significant levels of silicone oil (e.g., >10%) can lead to instability of the blend, with the silicone oil tending to separate out as a clear layer over time. That is, even though petrolatum itself is a self-structured oil (structured via long crystals formed by n-alkanes), if too much silicone is blended in (as in the >10% of the subject invention required for sensory improvements), the silicone will normally dilute the petrolatum structure (what we call "softening" the petrolatum) and separate out unless, as applicants have unexpectedly found, the silicone itself is properly structured (e.g., to "match" the properties of the petrolatum).

Unexpectedly, applicants have found that, if the silicone is structured with specific blending ratios of fatty acids (compared to traditional silicone gel thickener/gellants), the silicone in the petrolatum based composition will provide benefits of silicone e.g., less greasy and/or tacky feel of petrolatum) while avoiding the instability caused by silicone and petrolatum interaction, even at the levels of >10% silicone used to provide silicone benefits.

U.S. Pat. Nos. 6,264,963, 6,238,682, 5,849,314, 5,744,146, 5,643,899, 5,558,872, 5,494,657, 5,387,417, 5,308,526 describe generally low-water formulas that contain petrolatum; U.S. Pat. No. 5,643,899 describes compositions which contain cholesterol, acyl ceramides, ceramides, and essential and nonessential fatty acids. Some of these combinations are further enhanced by the addition of known moisturizers such as petrolatum and glycerine. However, there is no silicone oil in this formula.

As far as applicants are aware, there is no reference disclosing petrolatum compositions comprising silicone structured with the specific blending ratios of fatty acid as disclosed by the invention.

In another embodiment, the invention relates to cosmetic compositions comprising the petrolatum based composition.

BRIEF DESCRIPTION OF THE INVENTION

The present invention provides petrolatum based compositions comprising silicone structured by a specific blend of fatty acids. This allows the sensory benefits of silicone to be incorporated into the petrolatum (i.e., when silicone is used at levels of >10% by wt.) while maintaining stability (no separation) of the petrolatum. The key is to ensure the silicone is structured in the novel way described by this invention.

Specifically, the invention comprises a composition comprising:

(1) ≥50% to 90% by weight petrolatum
(2) >10% by weight (e.g., up to about 40% by wt.) silicone oil; and
  (a) blend of fatty acids (1-13%, preferably 3-6% by wt. total composition) which serve to structure the silicone comprising $C_{12}$ to $C_{30}$, preferably $C_{12}$ to $C_{22}$, more preferably $C_{12}$ to $C_{18}$ fatty acids wherein ratio of $C_{14}:C_{12}$ is about 1.18:1 to 2.0:1, ratio of $C_{16}$ to $C_{12}$ is about 1.8:1 to 2.5:1 and ratio of $C_{18}$ to $C_{12}$ is about 1.5:1 to 2.3:1, and wherein the "structured" silicone oil comprises 8 to 40%, preferably 10 to 32%, even more preferably 10 to 20% by weight fatty acids (e.g., fatty acid comprise 8 to 40% of mixture of fatty acid and silicone).

The compositions of the invention may be prepared by mixing all components (e.g., petrolatum, silicone, fatty acids) at high temperatures (typically about 75° C.), and then cooling to room temperature; or by pre-mixing silicone oil and fatty acids at high temperature (about 75° C.), cooling to room temperature (20-25° C.) and then mixing the structured silicone and petrolatum at high temperatures (about 75° C.).

In one embodiment of the invention, the petrolatum composition comprising silicone and structuring fatty acid blend further comprises copolymers bearing >70%, preferably >75% long chain (e.g., $C_{12}$ to $C_{30}$; preferably $C_{18}$ to $C_{24}$) alkyl groups. Copolymers of vinyl amide monomers, especially cyclic vinyl amide monomers (e.g., vinylpyrrolidone) and long chain (e.g., $C_{12}$-$C_{30}$) α-olefins (e.g., eicosane) are preferred. Typically, the copolymer is added to the petrolatum (before mixing with fatty acid structured silicone), the petrolatum is heated (65-75° C.) and cooled to room temperature. The petrolatum/polymer mixture is then combined with silicone and fatty acid blend.

When used at levels of about 0.01 to 3%, preferably 0.05 to 2%, the copolymers help reduce the viscosity of petrolatum so it is more readily spread. Spreading may occur, even if polymer is not used (if high levels of silicone are used to enhance spreading, higher levels of fatty acid blend are used to structure silicone and petrolatum mixture while ensuring the silicone does not phase separate), but use of the polymer permits less silicone to be used while still providing good spreadability. It should be noted that level of polymer used is believed to help form small, round crystals which reduce viscosity and promote spreadability. As level of polymer increases beyond a certain level, however, viscosity increases and spreadability is reduced. The combination of stable silicone (stabilized by fatty acid structuring) in reduced viscosity, higher spreading petrolatum (by using higher amounts of silicone; or lesser silicone and small amount of copolymers) helps yield an emollient which is easy to spread, while providing the moisturizing benefit of silicone and helping overall sensory (e.g., avoiding the greasy feel of petrolatum).

In a separate application, applicants disclose structured silicone oil which requires copolymers bearing high amounts of long chain alkyl. Copolymers of vinyl amide monomer, especially cyclic ones (e.g., vinylpyrrolidone), are preferred, the long chain α-olefins (e.g., eicosanes) are the long alkyl chains on the copolymer backbone. Such copolymers are not necessarily used as part of petrolatum composition of the subject invention but, if used, is preferably used in small amounts as noted above (e.g., to ensure better spreadability). In the separate application, the copolymer structured silicone may further comprise fatty acids.

In another embodiment, the invention relates to cosmetic compositions comprising the petrolatum compositions.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

Figure 1:
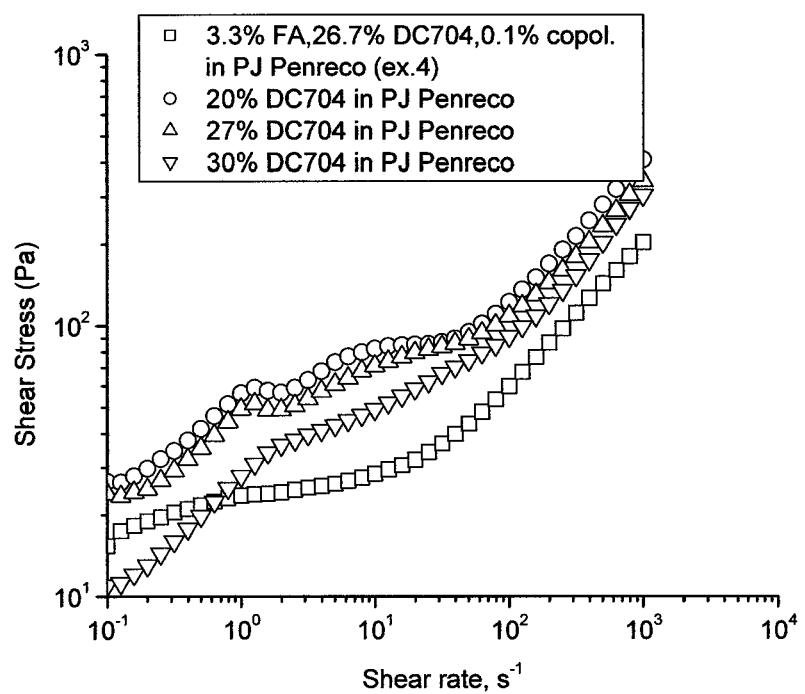
FIG. 1 shows flow curves for samples with no fatty acid and petroleum jelly mixed with silicone in different proportions (20, 27, 30%) The silicone is not structured with fatty acid. When fatty acids are added to silicone (3.3% fatty acid, 26.7% silicone fluid DC704, 0.1% vinylpyrrolidone copolymer, 69% petroleum jelly, see Example 4), flow curves shows the system has low viscosity (lower stress/ratio dependencies) compared to the samples (three comparatives) with no fatty acids and polymer added. Measurements were performed at 30° C. The fatty acids thus allow relatively large amounts of silicone to be used with petrolatum, while enhancing spreadability (lower viscosity) and providing nice sensory at these levels (e.g., lower stress beginning at shear rate of $1s^{-1}$ (10°) which it is believed to be better perceived by the consumer. While larger amounts of polymer might be used, they might provide less desirable sensory effects.

The present invention relates to petrolatum based compositions comprising silicone oils which are structured by a blend of specific chain-length fatty acid blended in defined ratios. In one embodiment, copolymers of vinylpyrrolidone and long chain ($C_{12}$-$C_{30}$) α-olefins are mixed with petrolatum before combining with silicone and fatty acids.

Specifically, the petrolatum compositions of this aspect of the invention comprise:

(1) greater than or equal to 50%, preferably 60 to 90% petrolatum (petrolatum is continuous phase and silicone phase is dispersed phase), wherein petrolatum is preferably more structured as opposed to less structured petrolatum liquid (wherein degree of structuring relates to elastic modulus since both structured and non-structured fluids can have the same viscosity);

(2) >10 to 40%, preferably 20 to 30%, more preferably 20 to 27% by wt. silicone oil (greater amount of silicone oil typically will require more fatty acid to build up viscosity; while lower viscosity may be beneficial for spreadability, especially if no optional polymer is used, higher viscosity helps maintain structure/stability); and (3) blend of fatty acids comprising $C_{12}$ to $C_{30}$, preferably $C_{12}$ to $C_{22}$, more preferably $C_{12}$ to $C_{18}$ fatty acids wherein ratio of $C_{14}$:$C_{12}$ is about 1.18:1 to 2.0:1, ratio of $C_{16}$ to $C_{12}$ is about 1.8:1 to 2.5:1 and ratio of $C_{18}$ to $C_{12}$ is about 1.5:1 to 2.3:1, and wherein the structured silicone oil comprises 8 to 40%, more preferably 10 to 32% by wt., more preferably 10 to 20% by wt. of fatty acids, wherein (1), (2) and (3) are mixed at 60-75° C., or wherein (2) and (3) are mixed at 60 to 75° C., cooled to about 20-25° C. and "structured" silicone so prepared is mixed with (1) at 60 to 75° C.

While it is preferred that the fatty acid be linear, saturated and non branched, in some embodiments the fatty acid may be partially unsaturated and/or branched. Of course, mixtures of all types of fatty acids may be used.

With regard to component (1), the elastic modulus (function of degree of structuring); measured at 30° C., frequency of 1 rad/s and strain amplitude γ=0.1% is G'=2000–3000 Pa for petroleum jelly Snow White® and G'=200-300 Pa for petroleum jelly liquid. The higher the G', the greater the structure.

The amount of fatty acids in the total formula may range from 1% to 13% by wt. total formula, preferably 3 to 10%, more preferably 3 to 6% by wt. Thus, for example, if there is 15% by wt. silicone oil in total composition and fatty acids comprise 20% of the structured oil, the fatty acids will comprise 3% by wt. total composition. As indicated above, the more silicone oil used, the more fatty acid that is needed to ensure structuring (e.g., stability) because the silicone when combined with petrolatum can cause phase instability. In theory, if a small enough amount of silicone is used, it can be evenly dispersed in the petrolatum and little, if any, fatty acid is needed since petrolatum is itself a structured oil. However, since a minimal amount (floor level) of silicon oil (>10%) is required to provide aesthetic benefits noted, the range of fatty acids noted are needed.

In a preferred embodiment, the petrolatum composition additionally comprises 0.01-3%, preferably 0.05-2% by wt. of copolymer carrying >70% long chain alkyl groups. Copolymers of vinylpyrrolidone and long chain ($C_{12}$-$C_{30}$, preferably $C_{18}$ to $C_{24}$) α-olefins are preferred. The polymers are typically mixed with petrolatum, and the petrolatum is heated (60-75° C.) and cooled to room temperature. The mixture is then combined with (2) and (3) as noted above. As indicated above, the polymers greatly enhance spreadability. As previously indicated, spreadability can also be improved using greater amounts of silicone, but this will typically require more fatty acid to ensure stability (e.g., lack of phase separation). When polymer is used, less silicone may be used while obtaining comparable spreadability to if more silicone but no polymer were used.

The petrolatum compositions in liquid gel and/or cleansing compositions, help provide the sensory feel associated with silicone.

The compositions are described in more detail below.

The first critical component of the compositions of the invention is petrolatum. By being a "petrolatum-based" composition is meant that the petrolatum comprises ≥50% petrolatum preferably 60 to 95% by wt. of the composition.

Petrolatum is a flammable, semi-solid mixture of hydrocarbons, obtained from petroleum, and having a melting point ranging from a little below to a few degrees above 100° F. (37° C.). It is colorless or pale yellow (when not highly distilled), translucent and devoid of taste and smell when pure. It is insoluble in water. One source of petrolatum, for example, is Petrolatum Snow White® from Penreco.

In general, petrolatum (either the less structured petroleum jelly having lower G', or the more structured PJ Snow White®, or PJ yellow) is structured due to the presence of n-alkanes (paraffins) with the fraction of paraffins depending on the distillation process and source of crude oil. Petrolatum which is more structured is preferred for purposes of this invention. Structuring is defined by the modulus and yield stress of the component. Elastic modulus, measured at 30° C., frequency 1 rad/s and strain amplitude of 0.1%, is G'=2000–3000 Pa for petroleum jelly Snow White®, for example, and G'=200–300 for the less structured petroleum jelly liquid.

A second critical component of the invention is the fatty acid structured silicone oil which will be used in the Petrolatum. Such oil has previously not been used, specifically at levels claimed, because of phase separation issues. The composition may be prepared by mixing petrolatum (PJ) (optionally comprising copolymer of vinylpyrrolidone and olefin, e.g., to help spreadability of the final composition), fatty acid and silicone at high temperature and, when cooled, structuring is obtained. As noted, the silicone and fatty acid may be heated and cooled to structure first as well (e.g., pre-mix). This fatty acid structured silicone material would then be heated to combine with PJ (and optional copolymer) and form the final composition at cooling.

A typical silicone oil is polydimethyl siloxane where two methyl groups attach to the silicon atom to form $(H_3C)[SiO(CH_3)_2]_nSi(CH_3)$ where n defines the length of the chain (n is typically >4). The upper limit of n is defined by the desirable viscosity of the silicone oil and may be 4 to 850, preferably 8 to 400.

Phenyl groups may be attached instead of methyl and would form, for example, Phenyltris (trimethylsiloxy)silane (one phenyl group), Tetraphenyl-dimethyldisiloxane (4 phenyl groups), Trimethyl Pentaphenyl Trisiloxane (5 phenyl groups). Alkyl groups generally, for example, or a combination of phenyl and other alkyl groups may be grafted to the silicone backbone. Silicone oils may be mixed together if necessary to achieve better sensory, spreadability, structuring and stability of cosmetic formulations.

Examples of silicone oils which are sold as commercial products include DC-704®, DC 556 and PH-1555 HRI cosmetic grade silicone fluids sold by Dow Corning. Preferred oils include DC704 or DC556.

Typically, large amounts of silicone would not be used in petrolatum based compositions because the petrolatum and silicone would phase separate. Applicants have unexpectedly found however that, if the silicone is structured with the right compositions and ratio of fatty acids, then ≥10% to 40%, preferably 20 to 30%, more preferably 20-27% silicone can be used (the more silicone used, the more fatty acid which is needed to ensure viscosity build-up of silicone and avoid separation issues). This has the benefit of alleviating the oil and/or greasy feel of the petrolatum (from the use of silicone) while also avoiding phase separation (because of the viscosity build-up and stability of the structured silicone).

Specifically, the fatty acids used to structure the silicone are $C_{12}$ to $C_{18}$ acids wherein ratios of larger chain to $C_{12}$ fatty acid are noted as below:

$C_{14}$:$C_{12}$ ratio (e.g., myristate to lauric): 1.18:1 to 2.0:1
$C_{16}$:$C_{12}$ ratio (e.g., palmitic to lauric): 1.8:1 to 2.5:1
$C_{18}$:$C_{12}$ ratio (e.g., stearic to lauric): 1.5:1 to 2.3:1.

Typically the total fatty acid as a percentage of the combination of fatty acid and the silicone is about 8 to 40%, preferably 10 to 32% of the two. Fatty acid represents 1-13%, preferably 3-10% of total formula.

When the specified fatty acids, silicone and petrolatum are combined, it is believed that the aspect ratio (the ratio of its longer dimension to its shorter dimension) of the crystals formed by fatty acids decreases in a manner which yields the observed increase in spreadability and decrease of tackiness and greasiness of petrolatum compositions. These attributes are enhanced even more (and there is believed even further decrease in aspect ratio of crystals formed by fatty acids) when 0.01-3% copolymers of vinylpyrrolidone and long chain olefins are also used.

The silicone oil, as noted, is preferably mostly or wholly structured with linear (non-branched), saturated fatty acids. In addition, the silicone may be combined with branched fatty acids and/or esters, as well as fatty alcohols having melting temperature above room temperature (defined at 20-25° C.), preferably above 35° C.

In another embodiment of the invention, the petrolatum-based, high silicone containing compositions of the invention (e.g., Examples 3-6 set forth in the Example section below) may be formulated into aqueous or anhydrous cosmetic compositions (e.g., body or facial care compositions) containing the petrolatum compositions structured with silicone (hereinafter, "PCSWS"), e.g., as part of the hydrophobic or fatty phase.

For example, most cosmetic preparations contain, at varying levels of concentration, a hydrophobic or fatty phase comprising a mixture of oil, a fat and/or wax. This is true, for example, for oil-in-water or water-in-oil emulsions, gels, oils for face and body care, milks and make-up products such as rouge or lipstick.

The PCSWS of the present invention may comprise 1 to 80%, for example of the total weight of the cosmetic composition. In the case of oil-in-water emulsion or body care compositions, PCSWS will more typically comprise 1 to 30%, preferably 2 to 15%, more preferably 2 to 10% by wt. of the cosmetic composition. Typically, water will comprise 70 to 99% by wt. preferably 80 to 90% of such compositions.

As compositions have less and less water, PCSWS may reach from 50 to 80% by wt. of the cosmetic. In a typical facial care application, PCSWS would comprise 40 to 70% by wt., preferably 45 to 65% by wt. of the cosmetic composition.

Other components which can be used in the hydrophobic or fatty phase of a cosmetic composition are vegetable or animal oils, synthetic oils, fats and/or wax.

Among vegetable or animal oils which may be used include almond oil, avocado oil, olive oil, jujube oil, sesame oil, soybean oil, colza oil, squalene, lanolin and derivatives of any of the above.

Among synthetic oils may be used are ethyl and isopropyl palmitate, alkyl myristates (isopropyl, butyl or cetyl myristate), triglycerides of octanoic or decanoic acid, cetyl ricinoleate, stearyl octanoate, hydrogenated polyisobutene, etc.

Among waxes which may be used are included carnauba wax, beeswax, ozokerite, candelilla wax, Montan wax and microcrystalline waxes.

The hydrophobic phase can also contain small amounts of fatty alcohol (e.g., typically 0.1-3% by wt., preferably 0.2-1% by wt.). These include long chain alcohols such as cetylic alcohol, stearylic alcohol, myristic alcohol, hydrostearylic alcohol, oleic alcohol and the like. In addition, the fatty phase may contain certain polymers, for example, polyvinyl pyrrolidine, typically in about 0.1-0.5% by wt.

As indicated, total amount of hydrophobic phase, including PCSWS, varies depending on whether cosmetic composition is mostly aqueous, somewhat aqueous or non-aqueous and may vary typically from 3 to 99% by wt. of the cosmetic compositions.

As noted, cosmetic compositions may be mostly aqueous or mostly anhydrous. The compositions may be fluid emulsions, lotions or more substantial emulsions. They may be, for example, milks or softening creams, milk or creams for hand care, makeup removing creams or milks, foundation bases, sunscreen milks or creams, artificial tanning milks or creams, milks or creams against perspiration, shaving creams or foams.

In one form, the compositions may comprise primarily (>50%, preferably >55% by wt.) hydrophobic phase, of which 80%-100% of said hydrophobic phase is PCSWS, and which take the form of a sunscreen oil (containing, for example, 0.1-3%, preferably 0.5-2% of a sunscreen which absorbs ultraviolet rays), a hair care oil, a body or hair care oil, a pre-shave or after shave oil, a bath oil, a gel, an ointment or a stick.

When in the form of cream or milk, the cosmetic composition is typically in the form of water-in-oil or oil-in-water emulsion wherein hydrophobic or fatty phase (including predominantly, 80-100% PCSWS) comprises 4 to 60% by wt., the water comprises 30 to 90% by wt. and an emulsifying agent comprise 0.5 to 20%, preferably 1 to 12% by wt. of cosmetic emulsion.

Among emulsifying agents non-limiting examples which may be used are as follows:

Fatty polyoxyethylene or polyglycerol alcohols, oxyethylene or non-oxyethylene alkyl sulfates, mixtures of at least one lanoate (e.g., magnesium, calcium, lithium, zinc or aluminum lanoate and hydrogenated lanoline and/or lanoline alcohol, esters of fatty acids and polyols such as glycerol or propylene glycol). Glycerol and propylene glycol are also functioning, for example, as humectants. Also can be used monoesters of fatty acids and polyoxyethylene sorbitan.

Cosmetic compositions may also include thickening agents and gellifying agents. These include, for example, magnesium and aluminum silicates; ether-vinylic/anhydride maleic copolymers (e.g., polymer sold as "Viscofas"®); carboxyvinylic polymers such as those sold under the name Carbopol®; or gels of organically modified montmorillonite and neutral oil such as for example the product Miglyol Gel®.

In addition, the cosmetic composition may comprise various other components, typically at levels of 0.1-3% by wt. including coloring agents, perfumes, preserving agents, chelators, UV filters, pigments, pearlizing agents, mineral or organic fillers and vitamins.

Protocol

Figure 3:
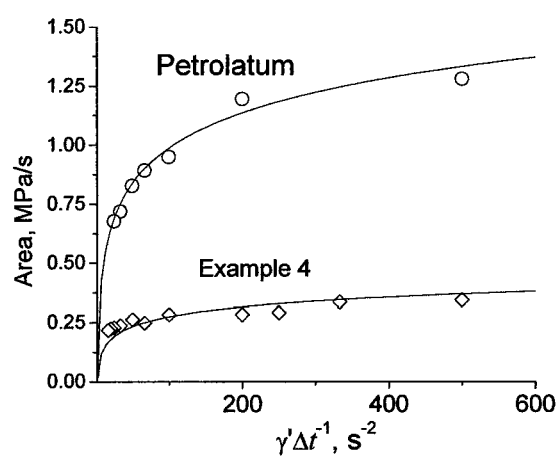
FIG. 3 shows dependency of area (A) under the thixotropic curve recorded at increasing shear rate versus γ' $Δt^{-1}$, $s^{-2}$ (shear rate divided by shear rate ramp interval Δt during which curve was recorded) again, for petrolatum versus petrolatum with "structured" fatty acid and the copolymer noted (Example 4). Each point on the curve represents the area under the upper curve in the thixotropic loops for various shear ramp rates recorded at 12-60 seconds (petrolatum-upper curve and Example 4). As seen, use of silicone "structured" with fatty acid and polymer significantly reduces the area under the stress shear rate curve. More specifically, the area under curve is a function of maximum shear rate (in our case max shear rate is $1000s^{-1}$) divided by time of recording the curve, Δt. The shorter the time, the more difficult to spread the oil, the area under the curve A varies from ~0 (infinite spreading time) to about 0.25 MPa/s for blend of Example 4 and from ~0 to about 1.25 MPa/s (less spreadable) for petrolatum alone. Thus, the figure shows that the polymer helps spreadability. It should be noted that, ideally, polymer comprises about 0.01 to 1%, preferably 0.9% by wt. of composition. Some polymer helps integrity of the composition and helps to stabilize. However, too much polymer leads to thickening. Specifically, initially small amount of polymer (0.1-3%) reduces viscosity of petrolatum because it is believed it lowers aspect ratio of crystals. At larger concentrations, this effect disappears and compositions simply become more viscous.

Greasiness and tackiness were initially evaluated from tactile experience and then using specially developed rheological testing that was found to correlate to tactile evaluation of spreadability of structured oils. Rheological measurements were performed using strain-controlled rheometer (ARES, TA Instruments) using plate-plate geometry (25 mm parallel plate, 1 mm gap). Thixotropic loops were recorded using shear rate ramp from $\gamma'=0\text{-}1000\ s^{-1}$ (ascending) and $1000\ s^{-1}$ to 0 (descending) recorded over different time intervals, $\Delta t=2\text{-}60\ s$ (FIG. 1), and area under the ascending curves were determined using integration tool of TA Orchestration Software. The areas under the stress curves A recorded at different time intervals $\Delta t$ were used as a measure of spreadability (FIG. 3). The spreadability was characterized using coefficient B in the empirical formula $A=B\ \log(\gamma'_{max}\Delta t^{-1})$ where $\gamma'_{max}$ is the maximum shear rate used to record thixotropic loops and $\Delta t$ is ramp time (e.g., $1000/\Delta t$). Thus, for example, the formula could be $A=B\ \log(1000/\Delta t)$, where B characterizes the spreadability of oils. The coefficient B was used as a spreadability index, being B=0.49 of pure Petrolatum Snow White (characterized as greasy and tacky) and B=0.137(with lower number indicating much better spreadability) for mixture of Petrolatum, silicone oil, fatty acids and polymer.

Figure 4:
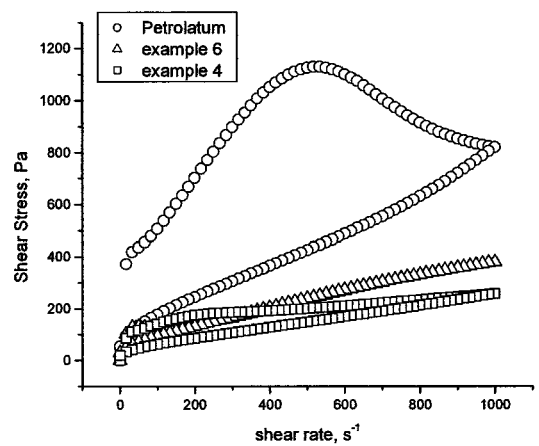
FIG. 4 is an example of thixtropic loops for petrolatum (two variants) versus Example 4 (fatty acid structured with polymer) and Example 6 (fatty acid structured without polymer). Loops are recorded at Δt=10 seconds. Again, this figure indicates that polymer is not required but, without it (triangles in figure), there is slightly less spreadability (measured by higher area under curve B which correlates with less spreadability). Areas under curve are 0.874 MPa/s for petrolatum (Peneco®), 0.234 MPa/s for Example 6 and 0.196 MPa/s for Example 4.
Figure 5:
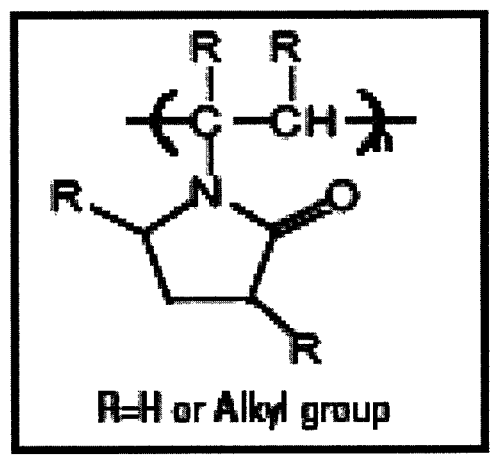
FIG. 5 is an example of a copolymer of vinylpyrididone and long, chain α-olefin.

The spreadability and skin feel of compositions were evaluated using trained expert panel. This panel consisted of five (5) scientists who have been working with these materials over the course of several years and made and/or sampled hundreds of formulations made in the laboratories. The panelists/scientists were asked to rate the compositions as more or less spreadable, tacky and greasy. The compositions were rated on a scale of 1 to 5 (e.g., 5 being the most greasy or the least spreadable and being 1 the best) and results on spreadability and feel correlated to rheological evaluation of spreadability (FIGS. 2-4), as well as feel.

Physical stability of best representatives was evaluated visually and, when evaluated over three months at room temperature and at 45° C. in the oven, no phase separation was observed. At this temperature the composition was found to exist below the cloud point. The "small" crystals were in equilibrium with the oil (liquid) phase. The cooled formulation was stable and showed no phase separation.

Flow curves were taken using parallel plates (25 mm) at 1 mm gap, at T=30° C. Initial and final shear rate were 0.1 and $1000\ s^{-1}$, respectively; 10 data points per decade. For each shear rate, the measurement time was 10 seconds and the interval between the measurements were 5 seconds.

EXAMPLES

Comparative Examples A to G and Example (Silicone Pre-Mixes)

The petrolatum compositions of the invention may be made by pre-forming the "structured" silicone composition (i.e., silicone plus fatty acid composition) and then combining with petrolatum to form final petrolatum composition; or by combining fatty acid, silicone and petrolatum at once, both methods as described in the specification above. Preferably, the silicone is pre-structured before combining with petrolatum, however.

When fatty acid structured silicone is used in petrolatum composition, (i.e., assuming the right ratio of fatty acids is used in the preparation), the resulting petrolatum compositions are thin (not rheologically "pasty"), fluffy, easily spreadable and have an oily rather than greasy feel.

Spreadability is defined by coefficient "B" in the empirical formula established for petrolatum and its mixtures $A=B\ \log (\gamma'_{max}\Delta t^{-1})$ (see protocol) where A is the area under the curve "shear stress-shear rate" recorded during the time interval $\Delta t$ and $\gamma'$ max is the maximum shear rate defined in the ranges. The stress increases from 0 to certain value over 10 second interval, and this is what is referenced to as the "ramp". In principle, spreadability is characterized by the area under stress curve recorded by shear rate ranges from 0 to $1000\ s^{-1}$ over time 10 s (10 seconds), i.e., the ramp.

In order to show the differences between a silicone structured by single or pairs of fatty acid, for example, compared to the specifically defined ratio of $C_{12}$, $C_{14}$, $C_{16}$ and $C_{18}$ of the invention, applicants prepared the following comparatives A-G:

| Composition, % | A | B | C | D | E | F | G |
|---|---|---|---|---|---|---|---|
| Lauric acid | 16 | 16 | 32 | 16 | | | 5.4 |
| Myristic acid | 16 | | | | 32 | | |
| Palmitic acid | | | | 16 | | | |
| Stearic acid | | 16 | | | | 32 | 26.6 |
| DC704 (silicone fluid) | 68 | 68 | 68 | 68 | 68 | 68 | 68 |

A description of the final silicone product for each example is noted below:

A solidified into rather fragile entity (initially rigid, but easily broken) which became grainy-like after enough force was applied (e.g., preferably with spatula).

B solidified into rather hard entity which became rather hard creamlike after enough force was applied.

C solidified into rather fragile entity which became liquid with gel particles after enough force was applied.

D solidified into rather hard entity which became hard cream like after enough force was applied.

E solidified into rather hard entity which became hard cream like after enough force was applied.

F solidified into too hard entity which becomes mica like flakes stacked together after enough force was applied.

G solidified into very hard entity which became rather soft after sufficient force was applied.

In every case A to G, the fatty acid ratio of fatty acids was outside that required by the claims and resulting silicone was flawed (e.g., not "structured" as per the invention) as described in each of the various ways noted. For example, they didn't have good spreadability and other gel properties such as those of our invention.

By contrast, applicants also prepared Examples 1 and 2 as noted below with description of the final silicone noted beneath:

| Composition, % | 1 | 2 |
| --- | --- | --- |
| Lauric acid | 3.25 | 2.1 |
| Myristic acid | 3.85 | 3.8 |
| Palmitic acid | 4.05 | 4.7 |
| Stearic acid | 3.85 | 4.5 |
| DC704 (silicone) | 85 | 84.9 |

1. Silicone oil was structured even with only 15% of fatty acids; the mixture appeared to be thin and creamy, easily spreadable, and having an oily secondary feel. Example 1 can also be described as a homogenous structured oil with thin creamy (primary) feel on skin and secondary oily feel.
2. No separation was observed, white homogeneous structured oil with thin creamy (primary) feel on skin and secondary oily feel.

As seen, compositions 1 and 2 of the invention had a spreadable rheology as desired by invention. In addition, because of silicone, they have desirable oily feel.

Examples 1 and 2 were easily spreadable. Further, when used in petrolatum compositions, the fatty acid structured silicone oil did not phase separate from petrolatum (i.e., because of fatty acid structuring).

Examples 1 or 2 above did form a gel but, it should be noted, are not intended to be representative of the petrolatum composition of the claim. They are intended only to demonstrate the ability of fatty acids to form gel in presence of silicone oil.

Examples 3-6

Petrolatum Composition Plus Structured Oil

The invention comprises petrolatum composition comprising the structured silicone described in the specification and examples above. As indicated, the structured silicone may be prepared separately (preferred) or not.

In Examples 3-5 below, the petrolatum composition further comprises 0.05 to 2% of a copolymer of vinylpyrrolidone and long chain α-olefin (e.g., Ganex® V-220). Example 6 has no polymer. In the examples, petrolatum, copolymer (if any), silicone oil and fatty acids are all mixed and heated together. Examples of the compositions are set forth below:

| Composition, % | 3 | 4 | 5 | 6 |
| --- | --- | --- | --- | --- |
| Petrolatum Snow White (Penreco) | 69.9 | 69.9 | 69.9 | 70 |
| 0.01-3, preferably 0.05-2.0% Ganex V-220 | 0.1 | 0.1 | 0.1 | 0 |
| Lauric acid | 0.63 | 0.46 | 0.42 | 0.63 |
| Myristic acid | 1.12 | 0.83 | 0.75 | 1.12 |
| Palmitic acid | 1.5 | 1.03 | 0.94 | 1.5 |
| Stearic acid | 1.35 | 0.98 | 0.89 | 1.35 |
| DC704 | 25.4 | 26.7 | 27.0 | 25.4 |

Examples 3, 4, 5 compositions were easily spreadable and stable.

Example 6, with no polymer, still provides silicone feel because of incorporation of silicone, but is slightly less spreadable, as measured by higher area under the value B (see protocol), presumably because of absence of polymer, which polymer helps spreadability.

Example H

In order to show that the final structured petrolatum composition must comprise right balance of fatty acid (and not simply a polymer in the absence of fatty acid), applicant prepared comparative H to contrast with examples 3, 4 and 5. This is set forth below:

| Composition, % | H |
| --- | --- |
| Petrolatum Snow White (Penreco) | 69.9 |
| Ganex V-220 | 0.1 |
| Lauric acid | 0 |
| Myristic acid | 0 |
| Palmitic acid | 0 |
| Stearic acid | 9.6 |
| DC704 | 20.4 |

Compositions H does not spread well in comparison to compositions 3, 4 and 5.

When no fatty acid is used (Comparative H) composition did not spread well. Further, when no vinylpyrrilidone polymer was used, composition did not spread well.

Example 7

In order to show that silicone not structured with fatty acid (versus fatty acid structured silicone of the invention) does not provide spreadable rheology like that of the invention, applicants measured the flow of three samples having silicone, but no fatty acid structure, mixed with petroleum jelly (at proportions of 20%, 27% and 30% silicone to petrolatum, respectively) compared to flow of mixture comprising 3.3% fatty acid mix, 26.7% silicone, 0.1% polymer and petrolatum. This is example 4 composition above. The flow curve results are set forth in FIG. 1.

The flow curve seen in FIG. 1 shows the fatty acid structured silicone system has lower viscosity (lower stress/rate dependency) compared with rates with no fatty acids and polymer added. The lower curves (less area with curve) correlates to less viscosity and higher spreadability. It is completely unpredictable that addition of fatty acid blends and silicone of invention would provide the properties observed of final petrolatum.

Example 8

Figure 2:
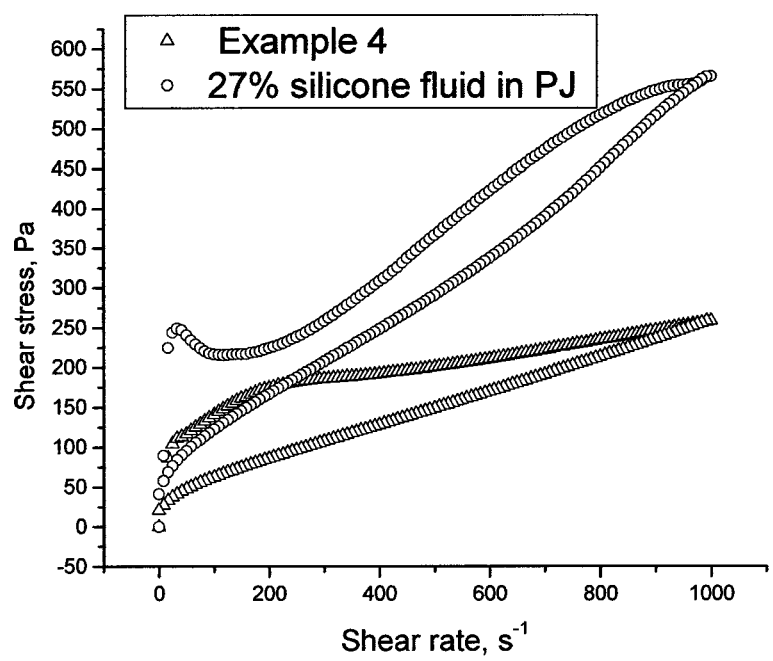
FIG. 2 is a comparison of thixotropic loops. The loops are plotted according to values obtained using thixotropic loop test. This test records the transient value of shear stress (y-axis) versus shear rate (x-axis), where transient viscosity is calculated as the transient value of shear stress divided by shear rate. The higher the area under the upper curve, the higher the viscosity wherein reduced viscosity (smaller area) is correlated with greater spreadability. Thixotropic loops were recorded at Δt=10 seconds (Δt is shear rate ramp interval during which curve was recorded) for petrolatum composition comprising unstructured silicone (i.e., not fatty acid structured) at level of 27% versus a petrolatum structured with 3.3% fatty acid blend (see Example 4). In general, the figures show that use of silicone oil "structured" with fatty acid and polymer (Example 4) significantly reduced viscosity of composition, (relative to unstructured) resulting in enhanced spreadability. This spreadability is due to silicone oil (which fluid reduces friction) as well as to the polymer (Ganex®), which is believed to make the n-alkane crystals more spherical-like. As noted, when used with petrolatum, it is preferred that silicone spreadability be accomplished most by fatty acid since sensory is better than if done with first silicone oil and petrolatum.

To again show enhanced spreadability of example of invention (Example 4) to silicone oil not structured with fatty acid, applicants compared thixtropic curve of example 4 to that of mix of 27% silicone mixed with petrolatum (see FIG. 2).

The procedure used was as described in protocol. As seen, fatty acid structured silicone (lower curve) had smaller area under the curve, an indication of superior spreadability.

Example 9

To again show superior spreadability, applicants measured dependency of area versus $\gamma'$ $\Delta t^{-1}$, $s^{-2}$, as shown in FIG. 3. Example 4 (area under curve a) had much better spreadability then comparative H.

Specifically, the fatty acid structured composition (Example 4) has significantly reduced area under the stress shear rate curve, an indication of both spreadability and lower viscosity in the range of shear rate measured.

Example 10

To show that polymer enhances spreadability even more, applicants measured thixotropic loops for composition comprising fatty acid with polymer (Example 4) versus one with fatty acid and no polymer (Example 6).

As seen from the area under the curve, example with polymer is even more spreadable than that without.

Example 11

In order to demonstrate the utility of the Petrolatum composition comprising structured silicone, applicants prepared the following compositions for body care (Example A) and facial care (Example B).

A)

| Ingredient | % by Weight |
|---|---|
| Composition of Example 3: | 5 |
| PJ | 3.5 |
| Structured silicone* | 1.5 |
| Polymer | 0.2 |
| Alcohol | 0.73 |
| Emulsifier | 0.75 |
| Sunscreen | 1.25 |
| TiO$_2$ | 0.2 |
| EDTA | 0.04 |
| Humectant | 1.00 |
| Preservative | 0.2 |
| Vitamin | 1.25 |
| Water | Balance |

Structured silicone* Lauric acid - 0.032%;
Myristic - 0.056%;
Palmitic - 0.075%;
Stearic - 0.068%;
DC704 - 1.27%

B)

| Ingredient | % by Weight |
|---|---|
| Composition of Example 4: | 57 |
| PJ | 39.9 |
| Structured silicone** | 17.1 |
| Polymer | 0.2 |
| Alcohol | 0.73 |
| Emulsifier | 2.5 |
| Sunscreen | 1.25 |
| TiO$_2$ | 0.2 |
| EDTA | 0.04 |
| Humectant | 1 |
| Preservative | 0.2 |
| Vitamin | 1.25 |
| Water | Balance |

Structured silicone** Lauric acid - 0.26%;
Myristic - 0.47%;
Palmitic - 0.58%;
Stearic - 0.56%;
DC704 - 15.22%

The invention claimed is:

1. A composition comprising:
    (1) from about 50% to about 90% by weight petrolatum;
    (2) from about 10% to about 40% by weight silicone oil; and
    (3) blend of fatty acids which serve to structure the silicone oil comprising $C_{12}$ to $C_{30}$ fatty acids wherein ratio of $C_{14}:C_{12}$ is about 1.18:1 to 2.0:1, ratio of $C_{16}$ to $C_{12}$ is about 1.8:1 to 2.5:1 and ratio of $C_{18}$ to $C_{12}$ is about 1.5:1 to 2.3:1, and wherein the silicone oil comprises 8 to 40% by weight fatty acids; wherein the silicone oil of (2) and fatty acids of (3) are premixed at a temperature of about 75° C., mixture is cooled to room temperature to form a structured silicone and the structured silicone is then mixed with petrolatum at temperature of about 75° C.

2. A composition according to claim 1 wherein the structured silicone comprises 10 to 32% by wt. fatty acid.

3. A composition according to claim 2 further comprising copolymers bearing greater than 70% long chain alkyl.

4. A composition according to claim 3 wherein the copolymer comprises vinyl amide monomer and long chain alkyl are α-olefins having chain length $C_{12}$ or greater.

5. A composition according to claim 4 wherein copolymers are copolymers of vinylpyrrilidone and long chain alkyl are $C_{12}$ to $C_{30}$ alpha olefins.

6. A composition according to claim 3 wherein said copolymer is combined with petrolatum before combining with silicone oil fatty acids.

7. A composition according to claim 1 wherein the silicone oil is polydialkyl siloxane.

8. A composition according to claim 1 wherein the fatty acids of (3) are saturated, non-branched fatty acids.

9. A composition according to claim 1 additionally comprising linear or branched fatty acids/ester and/or fatty alcohols with melting temperature above 20-25° C.

10. A composition according to claim 1 wherein, after the structured silicone and petrolatum are combined at 75° C., the composition is cooled to room temperature.

11. A cosmetic composition comprising the composition of claim 1.

12. A body or facial care composition comprising 1% to 80% of the composition of claim 1.

* * * * *